(12) United States Patent
Cao et al.

(10) Patent No.: US 11,187,819 B2
(45) Date of Patent: Nov. 30, 2021

(54) IMAGE SENSOR BASED ON CHARGE CARRIER AVALANCHE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 16/854,035

(22) Filed: Apr. 21, 2020

(65) Prior Publication Data
US 2020/0249367 A1    Aug. 6, 2020

Related U.S. Application Data

(63) Continuation of application No. PCT/CN2017/108240, filed on Oct. 30, 2017.

(51) Int. Cl.
*G01N 23/04* (2018.01)
*G01T 1/24* (2006.01)
(Continued)

(52) U.S. Cl.
CPC ............... *G01T 1/248* (2013.01); *A61B 6/14* (2013.01); *A61B 6/50* (2013.01); *A61B 6/502* (2013.01);
(Continued)

(58) Field of Classification Search
CPC ... G01T 1/248; G01T 1/241; G01T 1/24; A61B 6/14; A61B 6/50; A61B 6/502;
(Continued)

(56) References Cited

U.S. PATENT DOCUMENTS 5,844,291 A * 12/1998 Antich .................. H01L 31/115
257/438
6,002,134 A    12/1999 Lingren
(Continued)

FOREIGN PATENT DOCUMENTS

CN       1427956 A      7/2003
CN     101030609 A      9/2007
(Continued)

OTHER PUBLICATIONS

PCT/CN2017/108240 ISA210 Mail Date Aug. 1, 2018.
PCT/CN2017/108240 ISA237 Mail Date Aug. 1, 2018.

*Primary Examiner* — Kiho Kim
(74) *Attorney, Agent, or Firm* — IPro, PLLC; Qian Gu

(57) ABSTRACT

Disclosed herein is an apparatus suitable for radiation detection. The apparatus may comprise a radiation absorption layer and a first electrode on the radiation absorption layer. The radiation absorption layer may be configured to generate charge carriers therein from a radiation particle absorbed by the radiation absorption layer. The first electrode may be configured to generate an electric field in the radiation absorption layer. The first electrode may have a geometry shaping the electric field so that the electric field in an amplification region of the radiation absorption layer has a field strength sufficient to cause an avalanche of the charge carriers in the amplification region.

16 Claims, 19 Drawing Sheets

(51) Int. Cl.
*A61B 6/14* (2006.01)
*A61B 6/00* (2006.01)
*H01L 27/146* (2006.01)

(52) U.S. Cl.
CPC .......... *G01T 1/241* (2013.01); *H01L 27/1461* (2013.01); *H01L 27/1462* (2013.01); *H01L 27/14659* (2013.01); *H01L 27/14689* (2013.01); *H01L 27/14698* (2013.01)

(58) Field of Classification Search
CPC ............. H01L 27/1461; H01L 27/1462; H01L 27/14659; H01L 27/14689; H01L 27/14698
See application file for complete search history.

(56) References Cited

U.S. PATENT DOCUMENTS

| | | | |
|---|---|---|---|
| 6,204,087 B1 * | 3/2001 | Parker | H01L 27/1446 257/E27.129 |
| 10,074,685 B1 * | 9/2018 | Bakowski Holtryd | H01L 27/14658 |
| 2008/0303112 A1 | 12/2008 | Uya | |
| 2012/0205523 A1 | 8/2012 | Assefa et al. | |
| 2015/0001615 A1 | 1/2015 | Yong et al. | |

FOREIGN PATENT DOCUMENTS

| | | | |
|---|---|---|---|
| CN | 102237416 A | | 11/2011 |
| JP | 2012119371 A | * | 6/2012 |
| JP | 2012119371 A | | 6/2012 |
| WO | 2017004824 A1 | | 1/2017 |

\* cited by examiner

IMAGE SENSOR BASED ON CHARGE CARRIER AVALANCHE

TECHNICAL FIELD

The disclosure herein relates to an image sensor, particularly relates to an image sensor based on charge carrier avalanche.

BACKGROUND

An image sensor or imaging sensor is a sensor that can detect a spatial intensity distribution of a radiation. An image sensor usually represents the detected image by electrical signals. Image sensors based on semiconductor devices may be classified into several types, including semiconductor charge-coupled devices (CCD), complementary metal-oxide-semiconductor (CMOS), N-type metal-oxide-semiconductor (NMOS). A CMOS image sensor is a type of active pixel sensor made using the CMOS semiconductor process. Light incident on a pixel in the CMOS image sensor is converted into an electric voltage. The electric voltage is digitized into a discrete value that represents the intensity of the light incident on that pixel. An active-pixel sensor (APS) is an image sensor that includes pixels with a photodetector and an active amplifier. A CCD image sensor includes a capacitor in a pixel. When light incidents on the pixel, the light generates electrical charges and the charges are stored on the capacitor. The stored charges are converted to an electric voltage and the electrical voltage is digitized into a discrete value that represents the intensity of the light incident on that pixel

SUMMARY

Disclosed herein is an apparatus comprising: a radiation absorption layer configured to generate charge carriers therein from a radiation particle absorbed by the radiation absorption layer; a first electrode on the radiation absorption layer; wherein a geometry of the first electrode is configured to generate an electric field in an amplification region of the radiation absorption layer, the electric field having a field strength sufficient to cause an avalanche of the charge carriers in the amplification region.

According to an embodiment, the apparatus further comprises a second electrode on the radiation absorption layer, the second electrode being opposite from the first electrode.

According to an embodiment, the second electrode is configured to collect charge carriers in the radiation absorption layer.

According to an embodiment, the second electrode is planar.

According to an embodiment, the second electrode comprises discrete regions.

According to an embodiment, the discrete regions of the second electrode extend into the radiation absorption layer.

According to an embodiment, the first electrode comprises a tip with a shape of cone, frustum, prism, pyramid, cuboid or cylinder.

According to an embodiment, the first electrode is configured to collect the charge carriers generated directly from the radiation particles or by the avalanche of charge carriers.

According to an embodiment, the first electrode is configured to concentrate the electric field.

According to an embodiment, the first electrode extends into the radiation absorption layer.

According to an embodiment, the apparatus further comprises an outer electrode arranged around the first electrode, and electrically insulated from the first electrode; wherein the outer electrode is configured to shape the electric field in the amplification region.

According to an embodiment, the outer electrode is not configured to collect charge carriers.

According to an embodiment, the outer electrode comprises discrete regions.

According to an embodiment, the amplification region comprises a doped semiconductor.

According to an embodiment, the doped semiconductor is in electrical contact with the first electrode.

According to an embodiment, the doped semiconductor has a non-zero concentration gradient of a dopant.

According to an embodiment, the radiation absorption layer has a thickness of 10 microns or above.

According to an embodiment, the radiation absorption layer comprises silicon.

According to an embodiment, the radiation absorption layer comprises an intrinsic semiconductor region.

According to an embodiment, the apparatus further comprises a passivation material configured to passivate a surface of the radiation absorption layer.

Disclosed herein in an apparatus comprising: a radiation absorption layer configured to generate charge carriers therein from a radiation particle absorbed by the radiation absorption layer; a first electrode on the radiation absorption layer, a geometry of the first electrode configured to cause avalanche of the charge carriers in an amplification region of the radiation absorption layer.

Disclosed herein is a method comprising: forming a doped region of a semiconductor substrate by doping a surface of the semiconductor substrate with dopants; driving the dopants into the semiconductor substrate by annealing the semiconductor substrate; controlling doping profile of the doped region by repeating doping and annealing the semiconductor substrate.

According to an embodiment, the semiconductor substrate comprises silicon.

According to an embodiment, the doped region has a non-zero concentration gradient of the dopant.

According to an embodiment, doping is done by dopant diffusion or ion implantation.

According to an embodiment, the method further comprises forming a screening layer on the surface of the semiconductor substrate before doping the substrate, wherein the screening layer is configured to retard entry of dopants into the semiconductor substrate.

According to an embodiment, the screening layer comprises silicon dioxide.

According to an embodiment, the method further comprises forming a first electrode on the semiconductor substrate, wherein the first electrode is in electrical contact with the doped region.

According to an embodiment, the first electrode comprises a tip with a shape of cone, frustum, prism, pyramid, cuboid, or cylinder.

According to an embodiment, the first electrode extends into the semiconductor substrate.

According to an embodiment, the method further comprises forming an outer electrode arranged around the first electrode, wherein the outer electrode is electrically insulated from the first electrode.

According to an embodiment, the outer electrode comprises discrete regions.

According to an embodiment, the method further comprises forming a second electrode on the semiconductor substrate, wherein the second electrode being opposite from the first electrode.

According to an embodiment, the second electrode is planar.

According to an embodiment, the second electrode comprises discrete regions.

According to an embodiment, the discrete regions of the second electrode extend into the semiconductor substrate.

Disclosed herein is a system suitable for laser scanning, the system comprising: a laser source configured to generate a scanning laser beam; a detector comprising the apparatus of any one of the apparatuses disclosed above, wherein the apparatus is configured to collect return laser signals after the scanning laser beam bounces off an object.

According to an embodiment, the detector further comprises a signal processing system configured to process and analyze the return laser signals detected by the detector.

Disclosed herein is a system comprising: the apparatus of any one of the apparatuses disclosed above; an X-ray source; wherein the system is configured such that the apparatus forms an image of an object using X-ray from the X-ray source that penetrated the object.

According to an embodiment, X-ray source generates soft X-ray photons.

According to an embodiment, the radiation absorption layer of the apparatus has an absorbance of at least 80% for soft X-ray.

According to an embodiment, the system is configured to conduct chest X-ray radiography, abdominal X-ray radiography, dental X-ray radiography, or mammography.

According to an embodiment, the system is configured to conduct computation computed tomography.

According to an embodiment, the system is a microscope.

Disclosed herein is a detector comprising: the apparatus of any one of the apparatuses disclosed above; an electronics layer bonded to the apparatus, the electronics layer comprising an electronic system configured to process electrical signals generated in the apparatus.

According to an embodiment, the electronic system comprises a voltage comparator configured to compare a voltage of the first electrode of the apparatus to a first threshold; a counter configured to register a number of radiation particles absorbed by the apparatus; a controller; a voltmeter; wherein the controller is configured to start a time delay from a time at which the voltage comparator determines that an absolute value of the voltage equals or exceeds an absolute value of the first threshold; wherein the controller is configured to cause the voltmeter to measure the voltage upon expiration of the time delay; wherein the controller is configured to determine the number of radiation particles by dividing the voltage measured by the voltmeter by a voltage that a single radiation particle would have caused on the first electrode; wherein the controller is configured to cause the number registered by the counter to increase by the number of radiation particles.

According to an embodiment, the electronic system further comprising a capacitor module electrically connected to the first electrode, wherein the capacitor module is configured to collect charge carriers from the first electrode.

According to an embodiment, the controller is configured to connect the first electrode to an electrical ground.

According to an embodiment, the controller is configured to deactivate the voltage comparator at a beginning of the time delay.

DETAILED DESCRIPTION

Charge carrier avalanche is a process where free charge carriers in a material are subjected to strong acceleration by an electric field and subsequently collide with other atoms of the material, thereby ionizing them (impact ionization) and releasing additional charge carriers which accelerate and collide with further atoms, releasing more charge carriers—a chain reaction. Impact ionization is a process in a material by which one energetic charge carrier can lose energy by the creation of other charge carriers. For example, in semiconductors, an electron (or hole) with enough kinetic energy can knock a bound electron out of its bound state (in the valence band) and promote it to a state in the conduction band, creating an electron-hole pair. One example of an electronic device using the charge carrier avalanche is an avalanche photodiode (APD), which uses charge carrier avalanche to generate an electric current upon exposure to light. An APD will be used as an example to describe the charge carrier avalanche but the description may be applicable to other electronic devices that use the charge carrier avalanche.

An APD may work in the Geiger mode or the linear mode. When the APD works in the Geiger mode, it may be called a single-photon avalanche diode (SPAD) (also known as a Geiger-mode APD or G-APD). A SPAD is an APD working under a reverse bias above the breakdown voltage. Here the word "above" means that absolute value of the reverse bias is greater than the absolute value of the breakdown voltage. A SPAD may be used to detect low intensity light (e.g., down to a single photon) and to signal the arrival times of the photons with a jitter of a few tens of picoseconds. A SPAD may be in a form of a p-n junction under a reverse bias (i.e., the p-type region of the p-n junction is biased at a lower electric potential than the n-type region) above the breakdown voltage of the p-n junction. The breakdown voltage of a p-n junction is a reverse bias, above which exponential increase in the electric current in the p-n junction occurs. An APD working at a reverse bias below the breakdown voltage is operating in the linear mode because the electric current in the APD is proportional to the intensity of the light incident on the APD.

Figure 1:
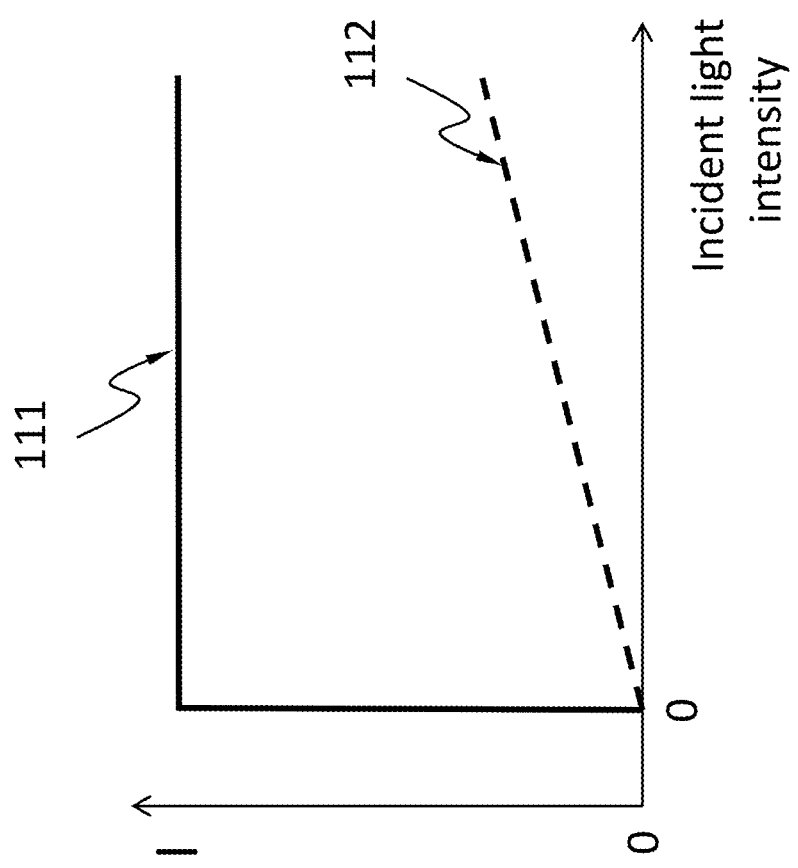
FIG. 1 schematically shows the electric current in an APD as a function of the intensity of light incident on the APD when the APD is in the linear mode, and a function of the intensity of light incident on the APD when the APD is in the Geiger mode.

FIG. 1 schematically shows the electric current in an APD as a function 112 of the intensity of light incident on the APD when the APD is in the linear mode, and a function 111 of the intensity of light incident on the APD when the APD is in the Geiger mode (i.e., when the APD is a SPAD). In the Geiger mode, the current shows a very sharp increase with the intensity of the light and then saturation. In the linear mode, the current is essentially proportional to the intensity of the light.

Figure 2C:
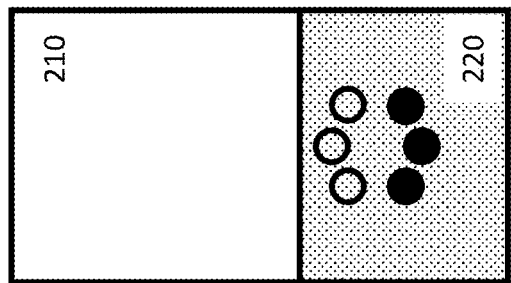
FIG. 2A, FIG. 2B and FIG. 2C schematically show the operation of an APD, according to an embodiment.
Figure 2B:
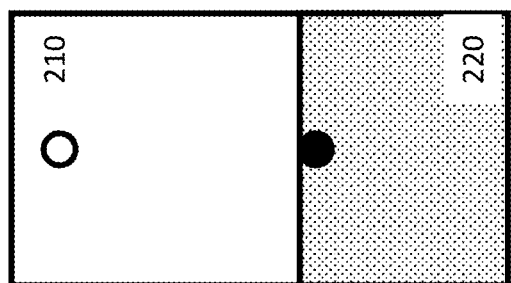
Figure 2A:
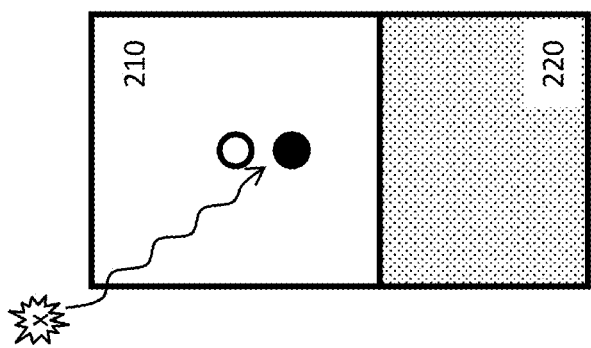

FIG. 2A, FIG. 2B and FIG. 2C schematically show the operation of an APD, according to an embodiment. FIG. 2A shows that when a radiation particle (e.g., an X-ray photon) is absorbed by an absorption region 210, one or more (100 to 10000 for an X-ray photon) electron-hole pairs maybe generated. The absorption region 210 has a sufficient thickness and thus a sufficient absorptance (e.g., >80% or >90%) for the incident photon. For soft X-ray photons, the absorption region 210 may be a silicon layer with a thickness of 10 microns or above. The electric field in the absorption region 210 is not high enough to cause avalanche effect in the absorption region 210. FIG. 2B shows that the electrons and hole drift in opposite directions in the absorption region 210. FIG. 2C shows that avalanche effect occurs in an amplification region 220 when the electrons (or the holes) enter that amplification region 220, thereby generating more electrons and holes. The electric field in the amplification region 220 is high enough to cause an avalanche of charge carriers entering the amplification region 220 but not too high to make the avalanche effect self-sustaining. A self-sustaining avalanche is an avalanche that persists after the external triggers disappear, such as radiation particles incident on the APD or charge carriers drifted into the APD. The electric field in the amplification region 220 may be a result of a doping profile in the amplification region 220, or the structure of the amplification region 220. For example, the amplification region 220 may include a p-n junction or a heterojunction that has an electric field in its depletion zone. The threshold electric field for the avalanche effect (i.e., the electric field above which the avalanche effect occurs and below which the avalanche effect does not occur) is a property of the material of the amplification region 220. The amplification region 220 may be on one or two opposite sides of the absorption region 210.

Figure 3A:
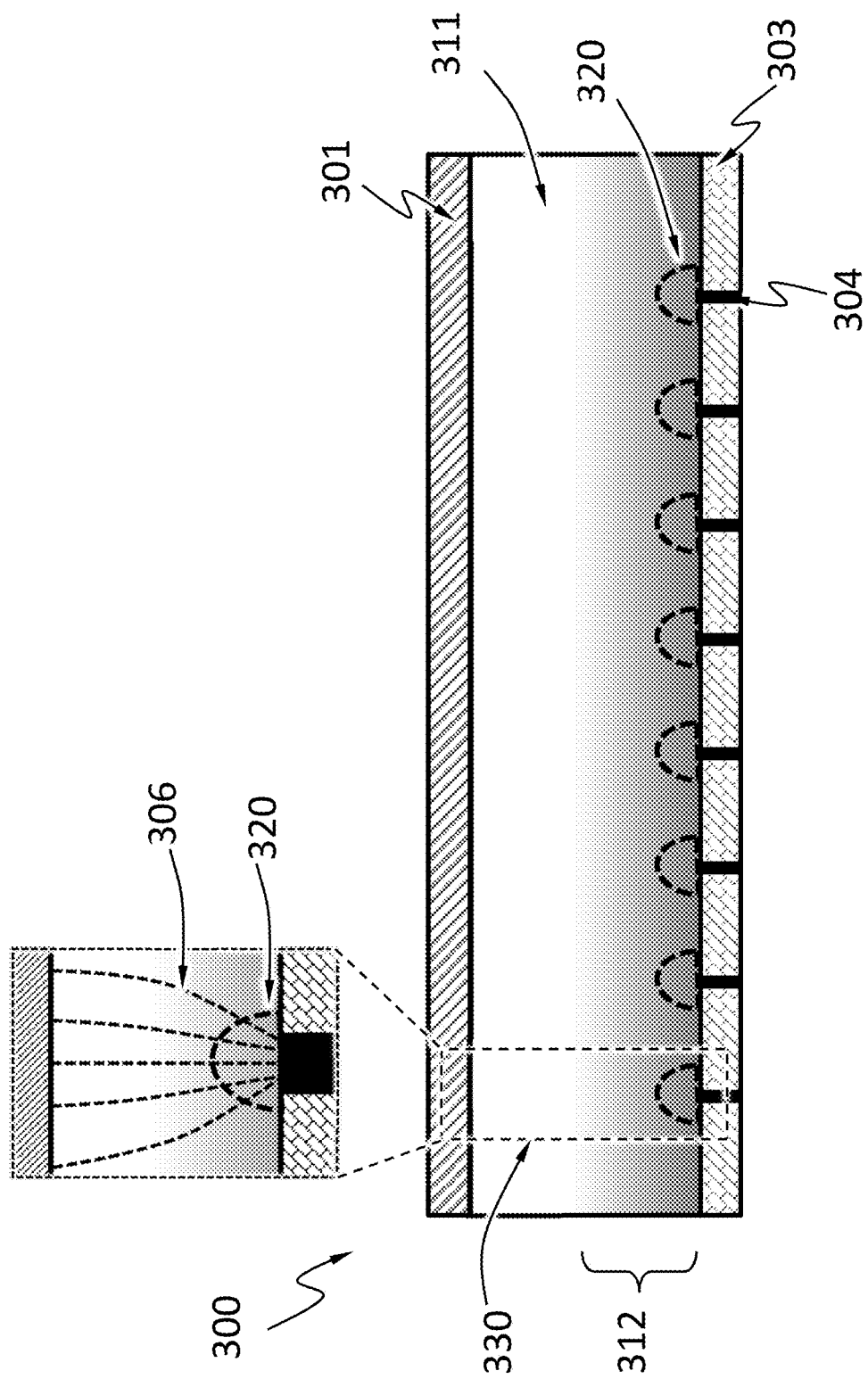
FIG. 3A schematically shows a cross-sectional view of an apparatus suitable for radiation detection, according to an embodiment.

FIG. 3A schematically shows a cross-sectional view of an apparatus 300 suitable for radiation detection, according to an embodiment. The apparatus 300 may comprise a radiation absorption layer 311 and one or more electrodes 304 on the radiation absorption layer 311. The radiation absorption layer 311 may be configured to generate charge carriers therein from a radiation particle absorbed by the radiation absorption layer 311. The one or more electrodes 304 may be configured to generate an electric field 306 in the radiation absorption layer 311. Each of the one or more electrodes 304 may have a geometry (e.g., a small tapered tip) shaping the electric field 306 so that the electric field 306 in one or more portions (i.e., one or more amplification regions 320) of the radiation absorption layer 311 has a field strength sufficient to cause an avalanche of the charge carriers (e.g., electrons or holes) in the one or more amplification regions 320. The charger carriers, either generated by the avalanche or directly from the radiation particles, drift to and are collected by the one or more electrodes 304 or a different electrode. The apparatus 300 may further include a passivation material 303 configured to passivate a surface of the radiation absorption layer 311 to reduce recombination of charge carriers at the surface. The apparatus 300 may further comprise a counter electrode 301 on the radiation absorption layer 311, the counter electrode 301 being opposite the one or more electrodes 304. The counter electrode 301 may be configured to collect charge carriers in the radiation absorption layer 311.

The radiation absorption layer 311 may comprise a semiconductor material such as silicon. The radiation absorption layer 311 may have a sufficient thickness and thus a sufficient absorbance (e.g., >80% or >90%) for incident radiation particles of interest (e.g., X-ray photons). The radiation absorption layer 311 may have a thickness of 10 microns or above.

Figure 3B:
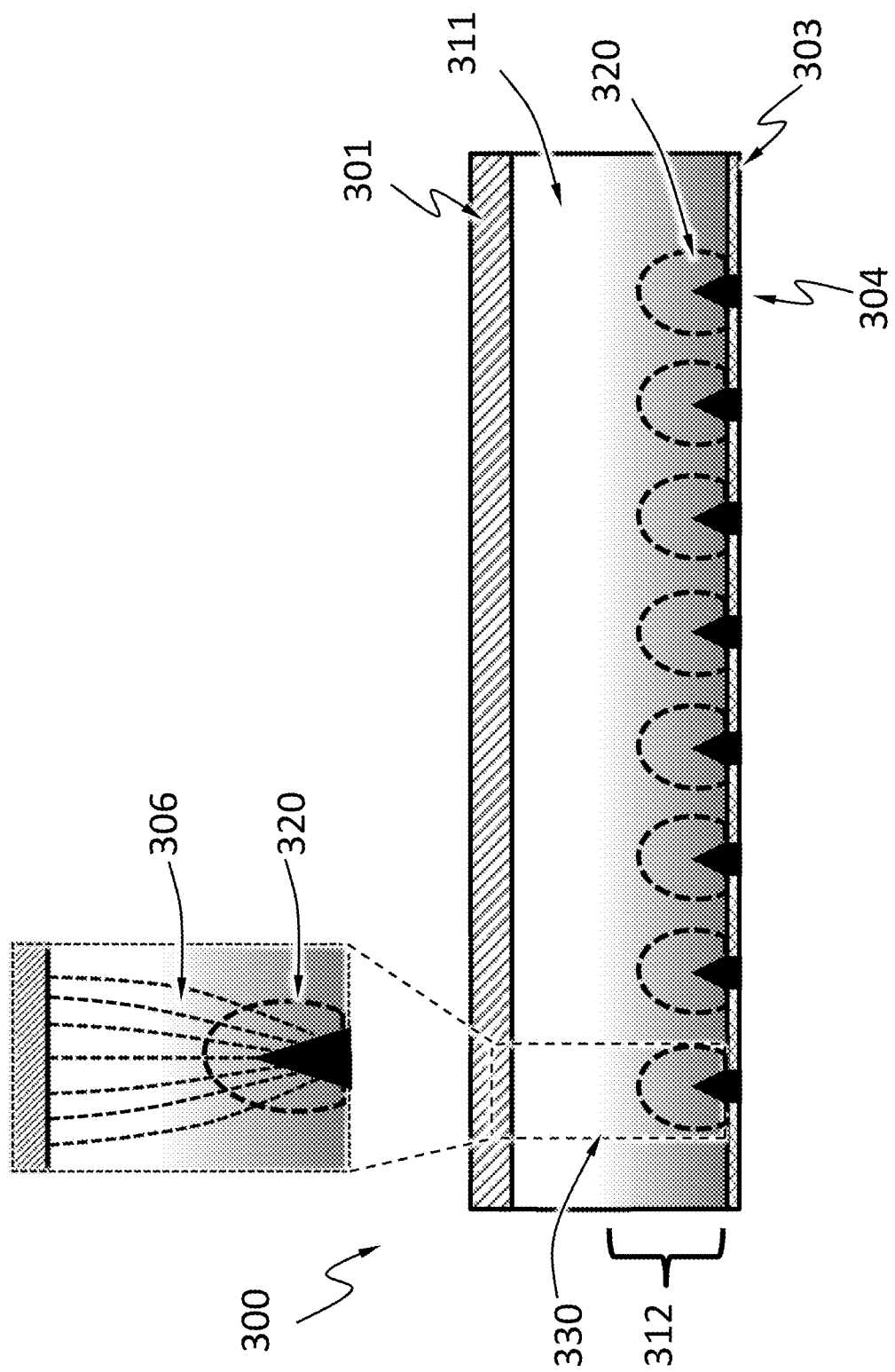
FIG. 3B shows a variant of the apparatus, according to an embodiment.
Figure 3C:
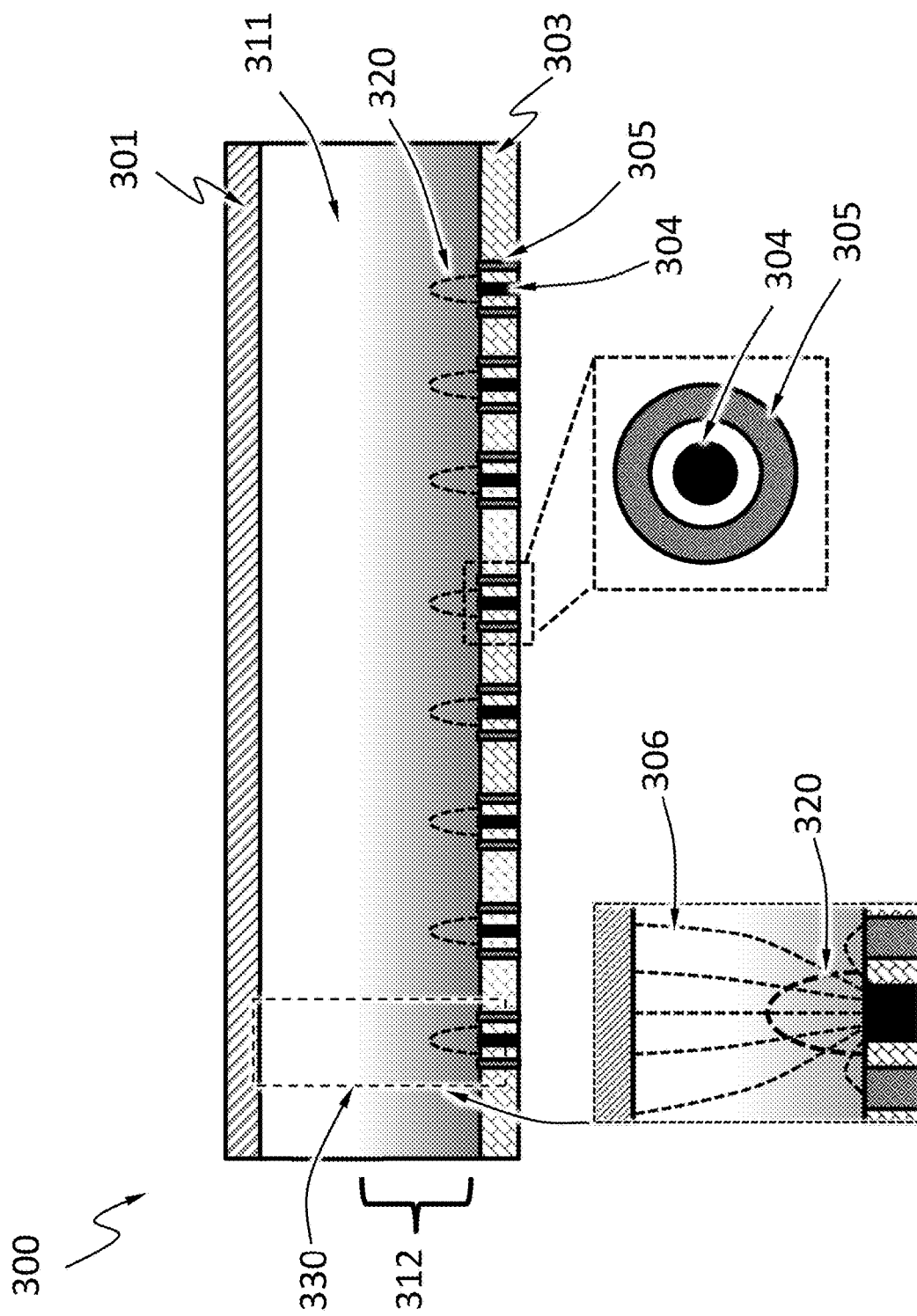
FIG. 3C shows a variant of the apparatus, according to an embodiment.

In an embodiment, the radiation absorption layer 311 may be an intrinsic semiconductor. In an embodiment, the radiation absorption layer 311 may comprise a doped region 312 that is lightly doped with a dopant. A semiconductor is considered to be lightly doped when the semiconductor contains a proportion of dopant to semiconductor atom being small enough so that the electronic states of the dopants at the Fermi level are localized (i.e., the band of the dopant may not overlap with the conduction or valence band of the semiconductor). For instance, lightly doped silicon may have a ratio of dopants to silicon atoms on the order of $1/10^{11}$. The doped region 312 may extend a few microns from a surface into the interior region of the radiation absorption layer 311, and may have a non-zero concentration gradient of the dopant. In the example of FIG. 3A-FIG. 3C, the concentration of the dopant gradually decreases from the surface to the interior region of the radiation absorption layer 311. The doped region 312 may be in electrical contact with the electrodes 304. In an embodiment, the doped region 312 may comprise discrete regions, each of which is around one of the electrodes 304.

The one or more electrodes 304 may comprise a conducting material such as a metal (e.g., gold, copper, aluminum, platinum, etc.), or any other suitable conducting materials (e.g., a heavily doped semiconductor). The one or more electrodes 304 may have small dimensions or a suitable shape so that the electric field 306 near the one or more electrodes 304 is concentrated. For example, the one or more electrodes 304 may comprise a tip with a shape of cone, frustum, prism, pyramid, cuboid, or cylinder, etc. In the example of FIG. 3A, the tip is flat and cylindrical. The flat tips of the electrodes 304 in FIG. 3A each have a contact area with the radiation absorption layer 311 small enough to have the electric field 306 near the tips become strong enough to cause avalanche of charge carriers near the tips. In other words, the strength of the electrical field 306 increases when approaching the electrodes 304, and the amplification regions 320 in FIG. 3A are regions around the tips of the electrodes 304 where the electrical field 306 is strong enough to cause avalanche of charge carriers. In an embodiment, the one or more amplification regions 320 correspond to the one or more electrodes 304 respectively. An amplification region 320 corresponding to one electrode 304 may not be joined with another amplification region 320 corresponding to another electrode 304. In an embodiment, the electrical field 306 is not strong enough to cause self-sustaining avalanche; namely, the electric field 306 in the amplification regions 320 should cause avalanche when there are incident radiation particles in the radiation absorption layer 311 but the avalanche should cease without further incident radiation particles in the radiation absorption layer 311.

When the radiation hits the radiation absorption layer 311, it may be absorbed and generate one or more charge carriers by a number of mechanisms. A particle of the radiation may generate 10 to 100000 charge carriers. One type (electrons or holes) of the charge carriers drift toward the amplification regions 320. The charge carriers may drift in directions such that substantially all (more than 98%, more than 99.5%, more than 99.9% or more than 99.99% of) charge carriers generated by a radiation particle incident around the footprint 330 of one of the electrodes 304 flow to the amplification region 320 corresponding to the electrode 304. Namely, less than 2%, less than 0.5%, less than 0.1%, or less than 0.01% of these charge carriers flow beyond the amplification region 320 corresponding to the electrode 304. When the charge carriers enter the amplification region 320, the avalanche effect occurs and causes amplification of the charge carriers. The amplified charge carriers can be collected through the corresponding electrodes 304, as an electric current. In the linear mode, the electric current is proportional to the number of incident radiation particles around the footprint 330 of the electrode 304 per unit time (i.e., proportional to the radiation intensity). The electric currents at the electrodes 304 may be compiled to represent a spatial intensity distribution of radiation, i.e., an image.

FIG. 3B shows a variant of the apparatus 300, where the electrodes 304 may extended into the radiation absorption layer 311, according to an embodiment. The portion of each of the electrodes 304 extending into radiation absorption layer 311 may have small dimensions or a suitable shape so that the electric field 306 near the portion is concentrated. For example, the portion may comprise a tip with a shape of cone, frustum, prism, pyramid, cuboid, or cylinder, etc. In the example of FIG. 3B, the tip is tapered, and the electric field 306 near the tapered tips become strong enough to cause avalanche of charge carriers near the tips. In other words, the strength of the electrical field 306 increases when approaching the portions of the electrodes 304, and the amplification regions 320 in FIG. 3B are regions around the portions where the electrical field 306 is strong enough to cause avalanche of charge carriers.

FIG. 3C shows a variant of the apparatus 300, where the apparatus 300 may further comprise one or more outer electrodes 305, according to an embodiment. The one or more outer electrodes 305 correspond to and locate around the one or more electrodes 304 respectively. The outer electrodes 305 are electrically insulated from the electrodes 304. For example, an insulation region (e.g., a portion of the passivation material 303) may exist in between an outer electrode 305 and its corresponding electrode 304.

In the example of FIG. 3C, the outer electrode 305 and its corresponding electrode 304 are coaxial. The outer electrode 305 may comprise a conducting material such as a metal (e.g., gold, copper, aluminum, platinum, etc.), or any other suitable conducting materials (e.g., a heavily doped semiconductor).

The outer electrode 305 may be configured to shape the electric field 306 in the amplification region 320 of the electrode 304 corresponding to the outer electrode 305, and the outer electrode 305 may not be configured to collect charge carriers. For example, the electric field 306 (e.g., its strength, gradient) may be tuned by introducing a voltage difference between the outer electrode 305 and its corresponding electrode 304. In an embodiment, the outer electrode 305 may have a same voltage with the counter electrode 301. In an embodiment, the outer electrode 305 may not necessarily be a ring as shown in FIG. 3C, but can have discrete portions.

In an embodiment, the counter electrode 301 may be planar, as shown in FIG. 3A-FIG. 3C. The counter electrode 301 may comprise discrete regions.

Figure 3D:
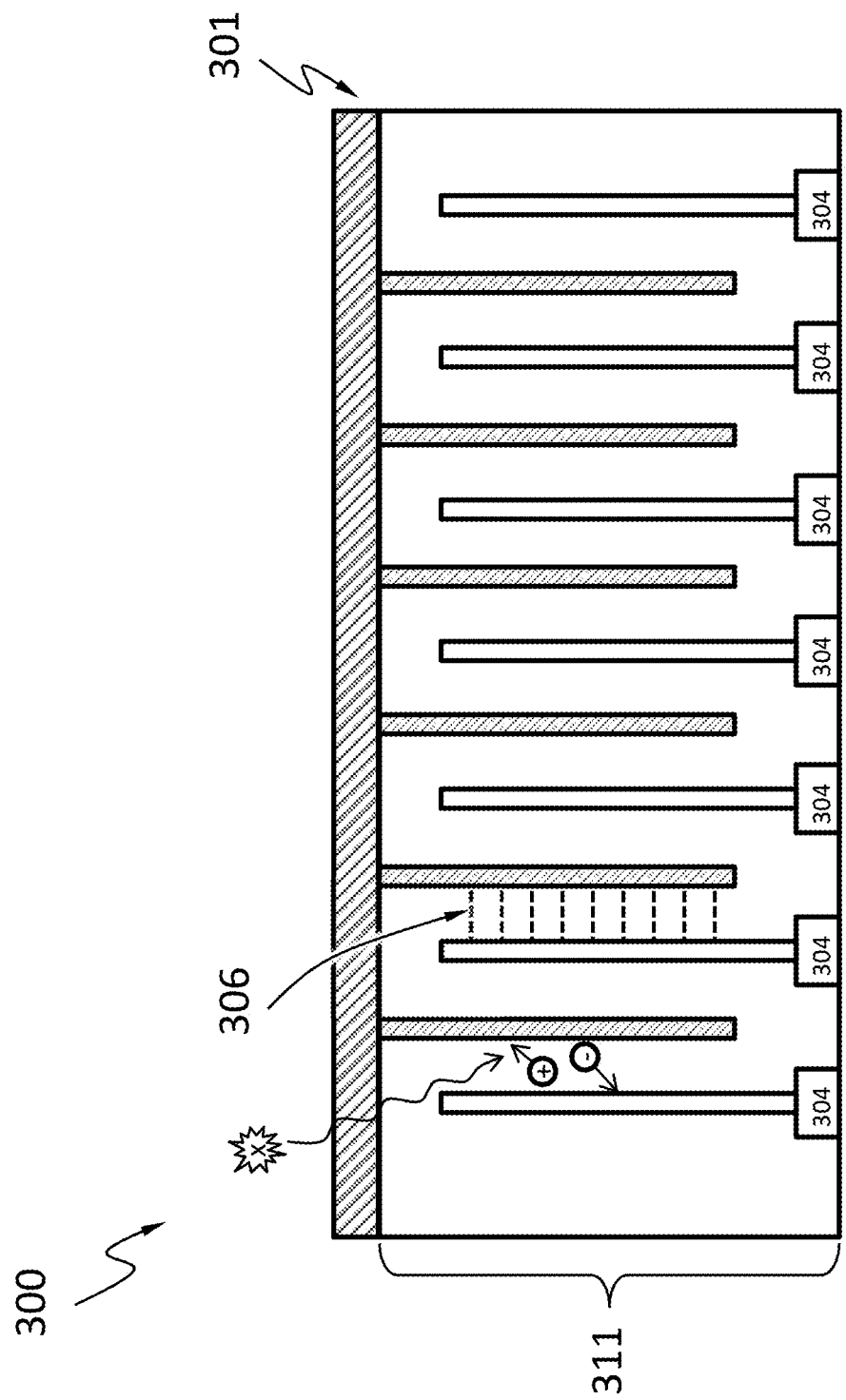
FIG. 3D shows a variant of the apparatus, according to an embodiment.

In an embodiment, as shown in FIG. 3D, the counter electrode 301 each may have geometry similar to one of the electrodes 304 and may extend into the radiation absorption layer 311. Avalanche of charge carriers may also take place in regions near the discrete regions of the counter electrode 301. The counter electrode 301 may comprise a conducting material such as a metal (e.g., gold, copper, aluminum, platinum, etc.), or any other suitable conducting materials (e.g., a heavily doped semiconductor).

In the example of FIG. 3D, the electrodes 304 and the counter electrode 301 have structures extending into the radiation absorption layer 311. For example, the structures may be holes are drilled into the radiation absorption layer 311 (e.g., by deep reactive-ion etching (DRIE) or laser and filled with a metal. The structures may form an Ohmic contact or a Schottky contact with the materials of the radiation absorption layer 311. The structures of the electrodes 304 and the structures of the counter electrode 301 may form an interdigitate pattern but should not be electrically short. Each of the structures of the electrodes 304 may be spaced by a short distance (e.g., 20 μm, 50 μm or 100 μm) from the nearest one of the structures of the counter electrode 301 to have the electric field 306 in between these structures become strong enough to cause avalanche of charge carrier in between these structures. In other words, the amplification regions 320 in FIG. 3D are regions in between these structure or near the tips of the structures where the electrical field 306 is strong enough to cause avalanche of charge carriers. These structures may help collecting charge carriers generated from a radiation particle or by the avalanche. The charge carriers only need to drift to one of these structures rather than the surfaces of the radiation absorption layer 311, thereby reducing the chance of recombination or trapping. The time for the charge carriers to be collected by these structures may be on the order of 0.1-1 ns.

Figure 4:
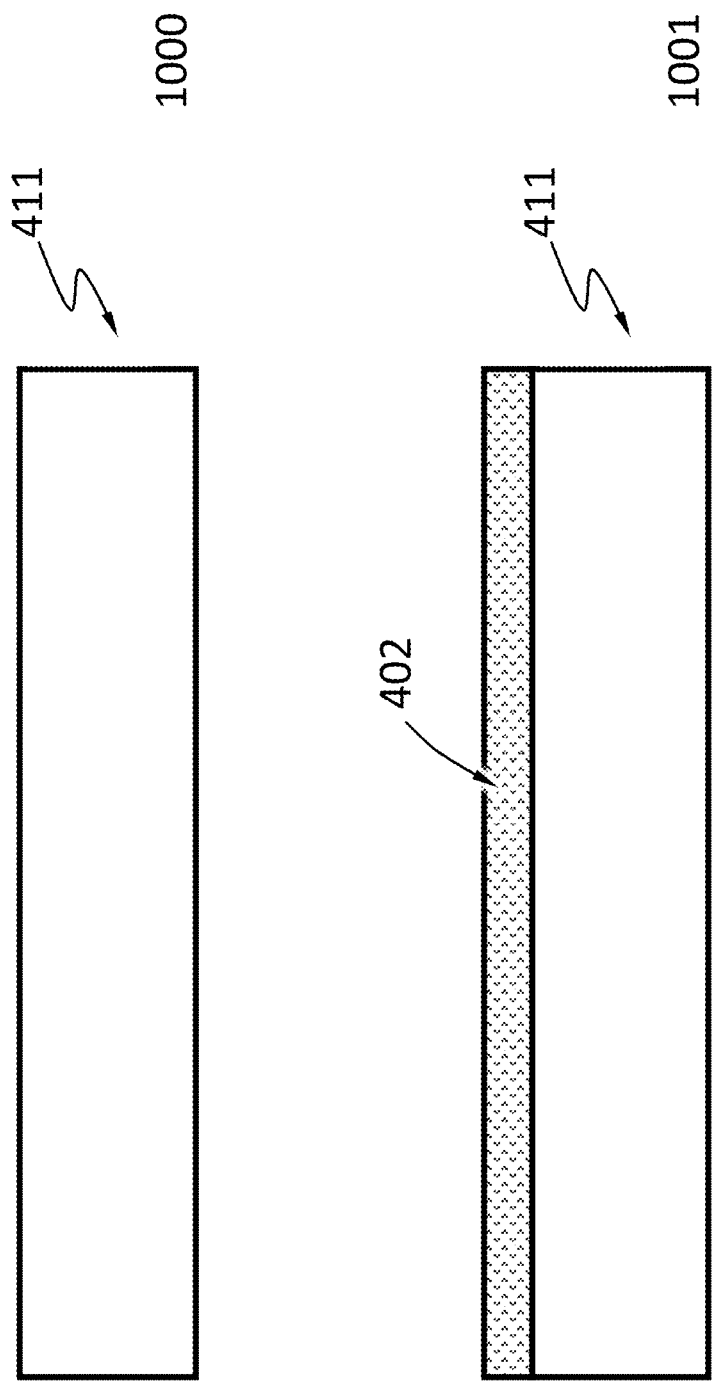
FIG. 4 schematically illustrates a process of forming the apparatus, according to an embodiment.
Figure 4:
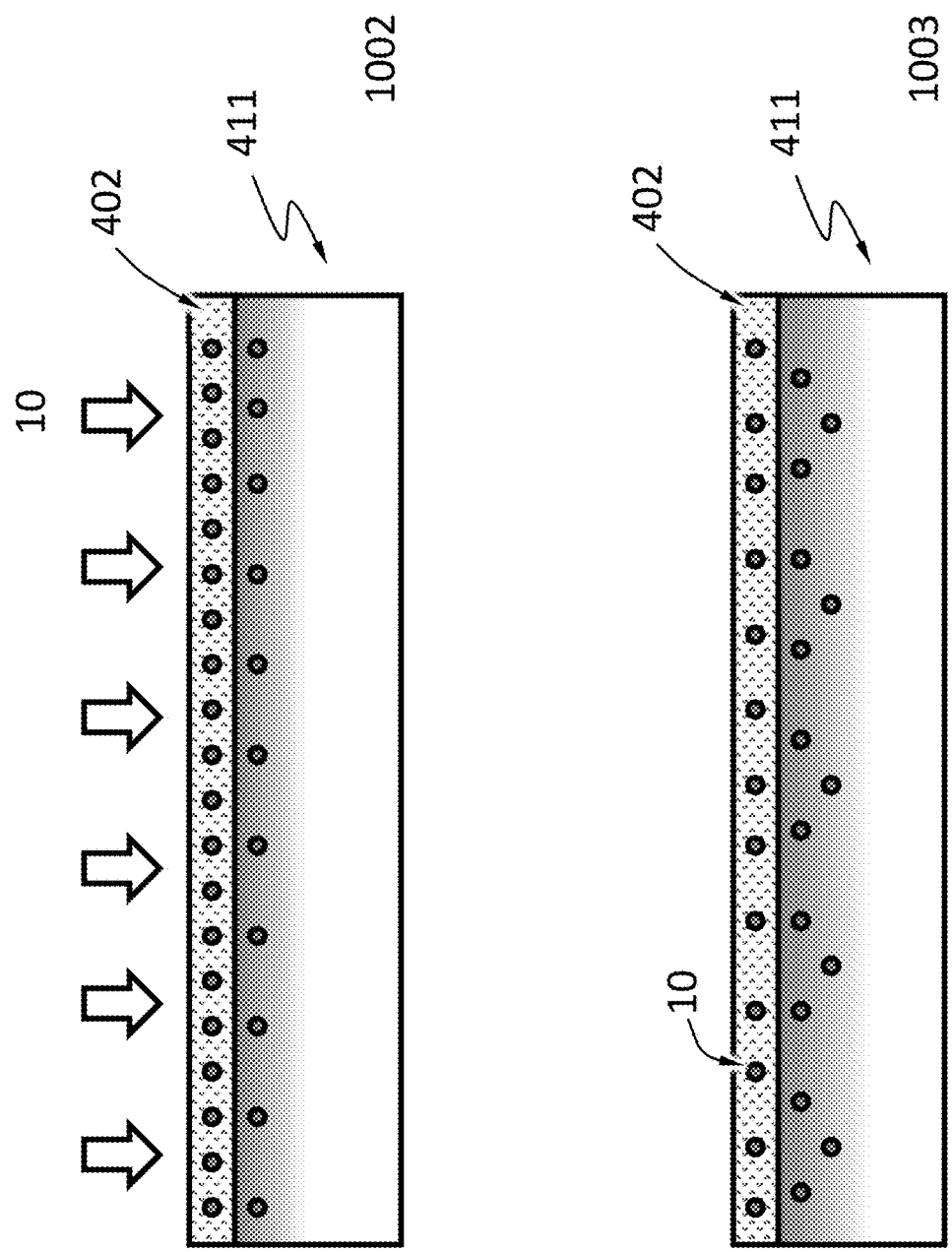
Figure 4:
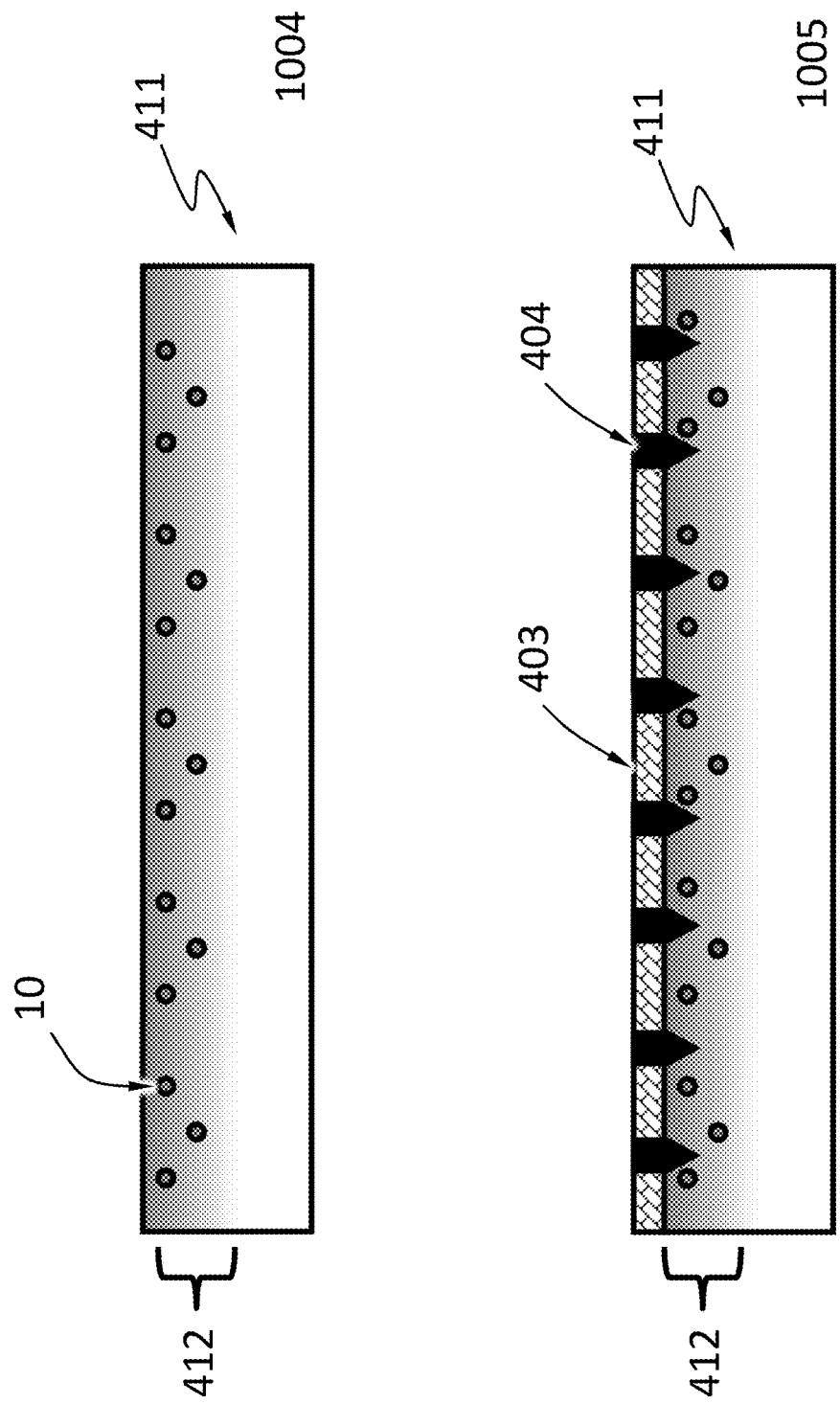
Figure 4:
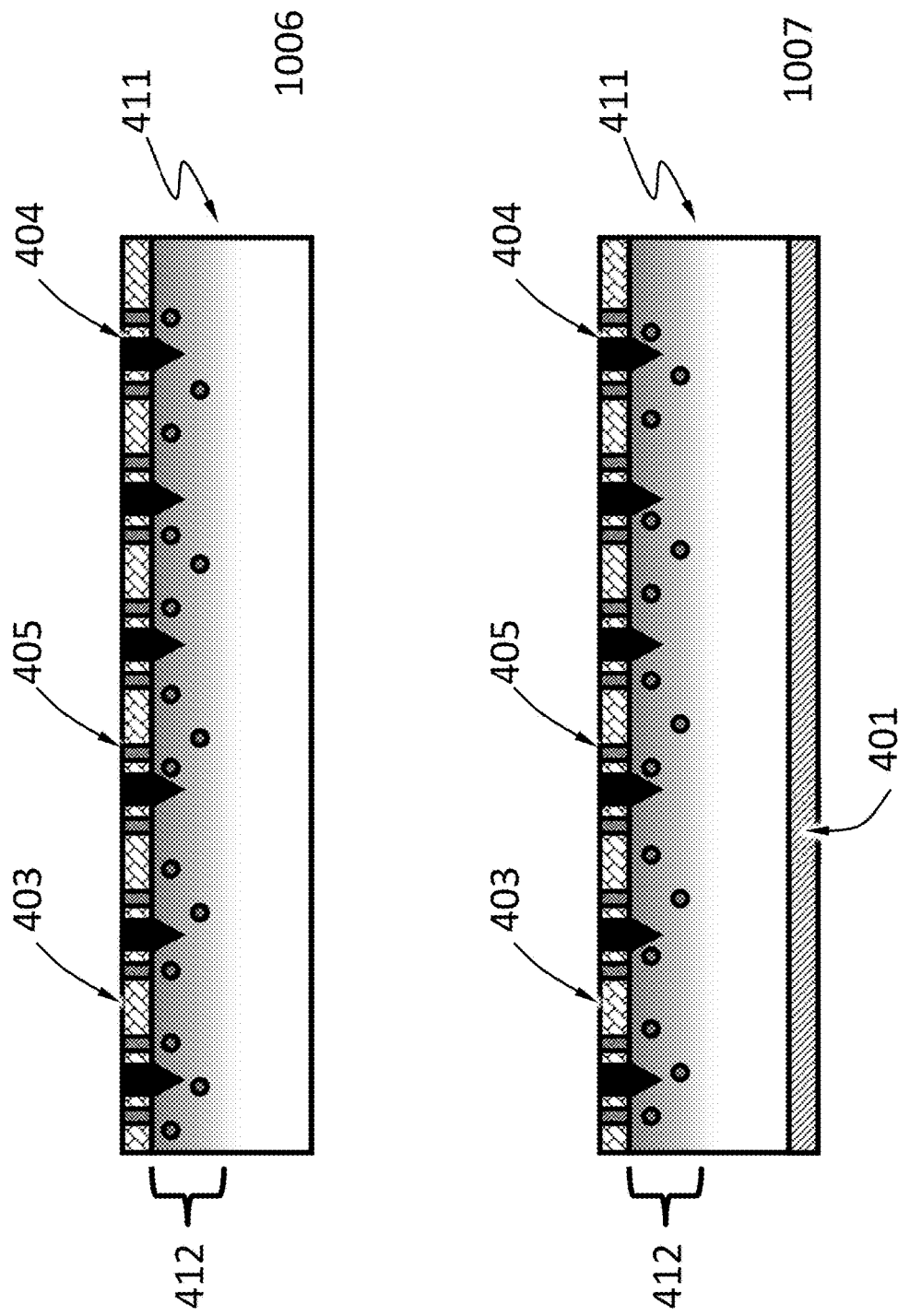

FIG. 4 schematically illustrates a process of forming the apparatus 300, according to an embodiment.

In step 1000, a semiconductor substrate 411 is obtained. The semiconductor substrate 411 may comprise an intrinsic semiconductor such as silicon. The semiconductor substrate 411 may have a sufficient thickness and thus a sufficient absorbance (e.g., >80% or >90%) for incident radiation particles of interest (e.g., X-ray photons). The semiconductor substrate 411 may have a thickness of 10 microns or above.

In step 1001-step 1003, the semiconductor substrate 411 may be doped to form a doped region 412 (shown in step 1004-step 1006). The doped region 412 may function as the doped region 312 of the radiation absorption layer 311 in FIG. 3A-FIG. 3C. In the example of FIG. 4, the doped region 412 to be formed is a continuous layer. In an embodiment, the semiconductor substrate 411 is a silicon substrate, the desired doped region 412 is lightly doped and have a non-zero concentration gradient of the dopant extending a few microns from the surface into the interior region of the semiconductor substrate 411. The concentration of the dopant may gradually decrease from the surface to the interior region of the semiconductor substrate 411.

In step 1001, a mask layer 402 is formed on a surface of the semiconductor substrate 411. The mask layer 402 may serve as a screening layer configured to retard entry of dopants into the semiconductor substrate 411 in the step 1002 of doping. The mask layer 402 may comprise a material such as silicon dioxide. The thickness of the mask layer 402 may be determined according to doping conditions in step 1002 and desired doping profile of the doped region 412 (shown in step 1004-step 1006) to be formed. The mask layer 402 may be formed onto the surface by various techniques, such as thermal oxidation, vapor deposition, spin coating, sputtering or any other suitable processes.

In step 1002, a surface of the semiconductor substrate 411 is light doped with a suitable dopant 10 by a doping technique such as dopant diffusion and ion implantation. The rate of dopant entering into the semiconductor substrate 411 may be controlled by the mask layer 402, the dose of dopants doped, and doping details such as the energy of the dopants during an ion implantation.

In step 1003, the semiconductor substrate 411 being doped is annealed to drive the dopants into the interior region of the semiconductor substrate 411. The dopants diffuse into the interior region at elevated temperatures (e.g., around 900° C.). The annealing duration may be prolonged to promote diffusion of the dopants into the interior region. The high-temperature environment of the annealing may also help anneal out defects of the semiconductor substrate 411.

Besides controlling the doping and annealing conditions, the doping (step 1002) and annealing (step 1003) may be carried out in a repeating manner for a number of times to form the doped region 412 with a desired doping profile.

In an embodiment, the doped region 412 may comprise discrete regions. The mask layer 402 may have a pattern with areas of different thicknesses. A portion of dopants can penetrate through the thinner areas of the mask layer and form discrete regions of the doped region 412, while the thicker areas of the mask layer prevent the dopants entering into the semiconductor substrate 411.

In step 1004, the mask layer 402 may be removed by wet etching, chemical mechanical polishing or some other suitable techniques.

In step 1005, electrodes 404 may be formed onto the semiconductor substrate 411. The electrodes 404 may function as the electrodes 304 of the apparatus 300. The electrodes 404 may be in electrical contact with the doped region 412. In the example of step 1005, the electrodes 404 each comprise a tapered tip extending into the semiconductor substrate 411. Forming the electrode 404 may involve forming a mask with openings on the surface of the semiconductor substrate 411 by suitable techniques such as lithography. Shapes and locations of the openings correspond to the footprint shapes and locations of the electrodes 404 to be formed. Recesses of desired shape and dimensions are formed into the surface of the semiconductor substrate 411 by etching portions of the substrate 411 uncovered by the mask. The etching process may be carried out by a technique such as dry etching (e.g., deep reactive-ion etching), wet etching (e.g., anisotropic wet etching), or a combination thereof. Conducing materials such as metal (e.g., gold, copper, aluminum, platinum, etc.) may be deposited into the recesses to form the electrodes 404 by a suitable technique such as physical vapor deposition, chemical vapor deposition, spin coating, sputtering, etc. The mask may be kept and server as a passivation layer of the surface of the substrate 411. In an embodiment, the mask may be removed and a passivation material 403 may be applied to passivate the surface of the substrate 411.

In optional step 1006, outer electrodes 405 may be formed around the electrodes 404. The electrodes 405 may function as the outer electrodes 305 in FIG. 3C. Forming the outer electrodes 405 may involve mask forming and metal deposition processes similar to the step 1005.

In step 1007, a counter electrode 401 may be formed on another surface of the semiconductor substrate 411. The counter electrode 401 may function as the counter electrode 301 of the apparatus 300. In the example of step 1007, the counter electrode 401 is planar and may be formed by depositing conducting materials such as metals onto the other surface of the semiconductor substrate 411 by a suitable technique such as vapor deposition, sputtering, etc.

Forming the apparatus 300 may comprise some intermediate steps such as surface cleaning, polishing, surface passivation, which are not shown in FIG. 4. The order of the steps shown in FIG. 4 may be changed to suit different formation needs.

Figure 5:
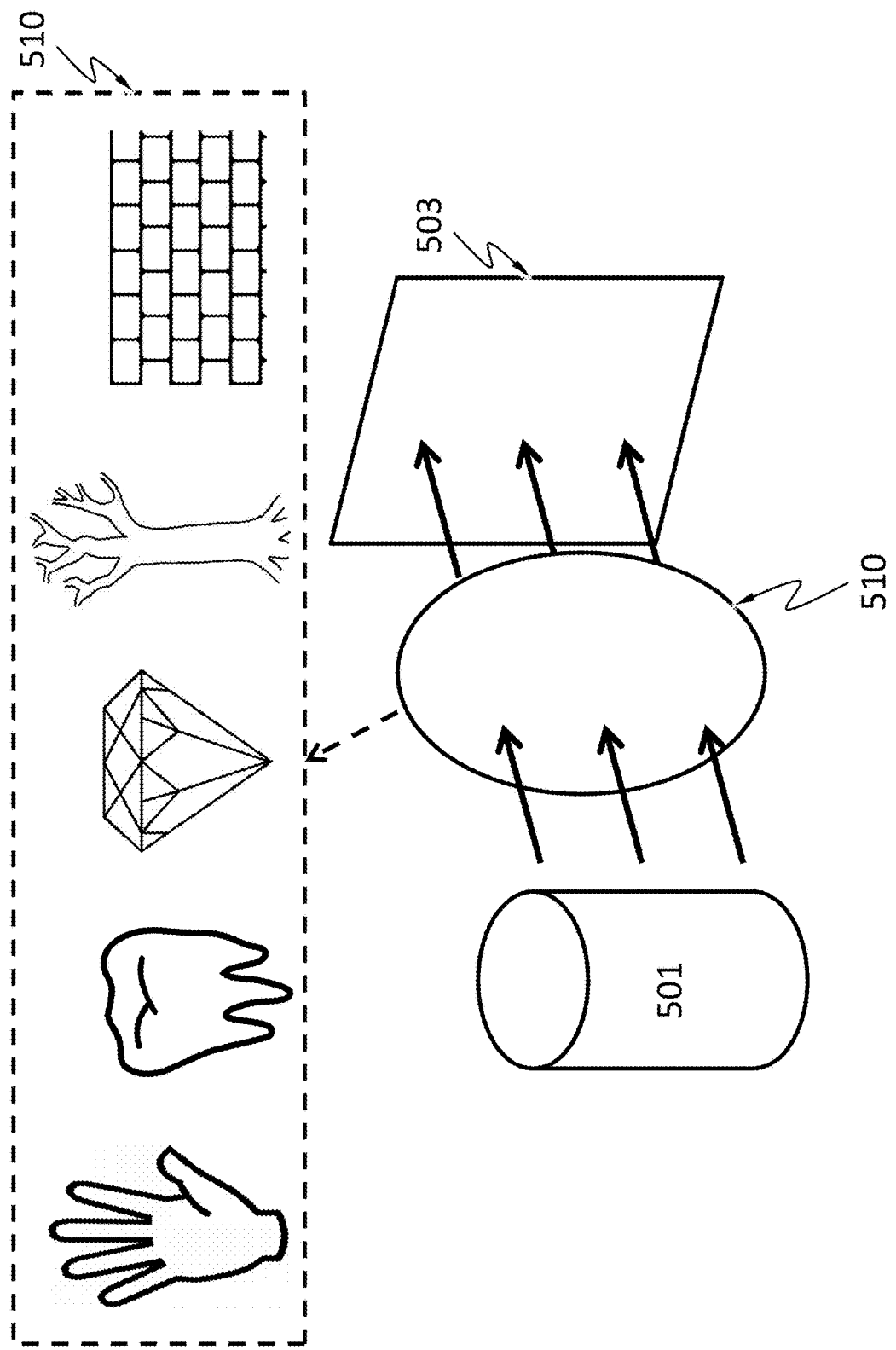
FIG. 5 schematically shows a system comprising an imaging sensor being an embodiment of the apparatus described herein.

FIG. 5 schematically shows a system comprising an imaging sensor 503 being an embodiment of the apparatus 300 described herein. The system comprises an X-ray source 501. X-ray emitted from the X-ray source 501 penetrates an object 510 (e.g., diamonds, tissue samples, a human body part such as breast), is attenuated by different degrees by the internal structures of the object 510, and is projected to the image sensor 503. The image sensor 503 forms an image by detecting the intensity distribution of the X-ray. The system may be used for medical imaging such as chest X-ray radiography, abdominal X-ray radiography, dental X-ray radiography, mammography, etc. The system may be used for industrial CT, such as diamond defect detection, scanning a tree to visualize year periodicity and cell structure, scanning building material like concrete after loading, etc.

Figure 6:
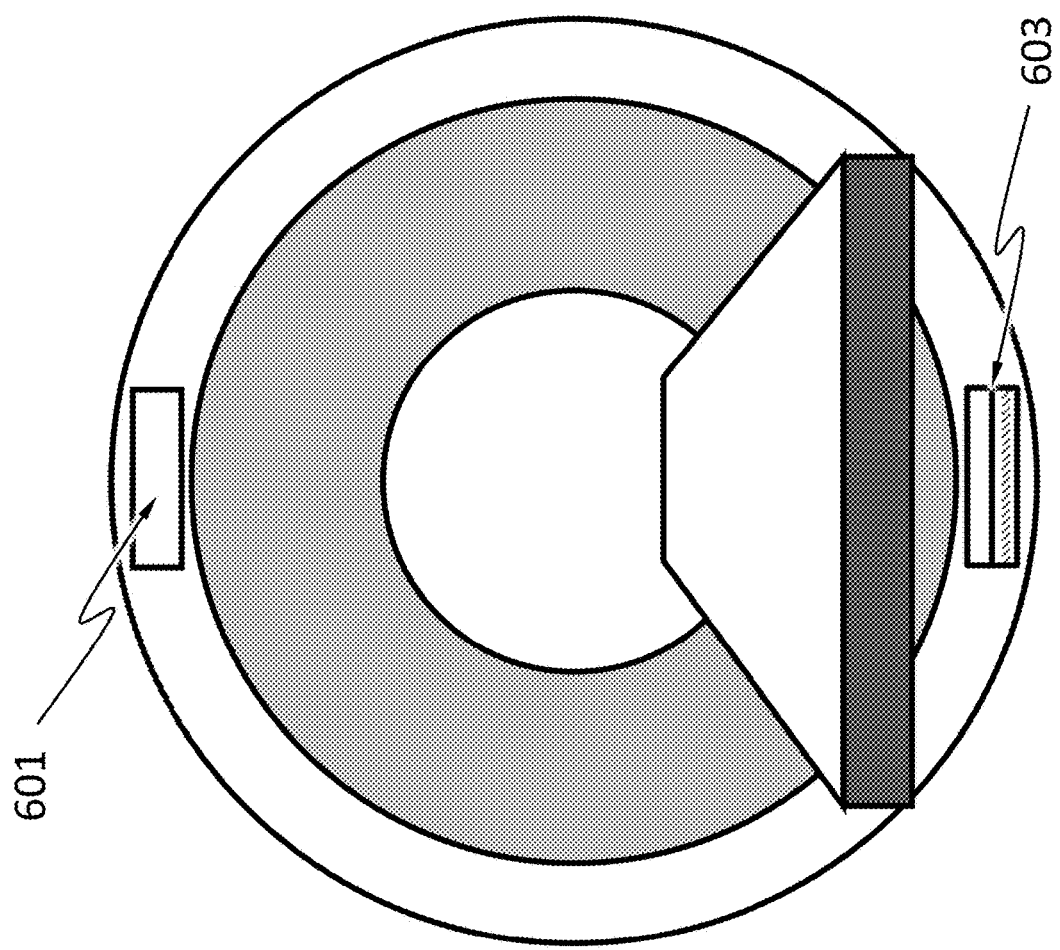
FIG. 6 schematically shows an X-ray computed tomography (X-ray CT) system.

FIG. 6 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the image sensor 603 being an embodiment of the apparatus 300 described herein and an X-ray source 601. The image sensor 603 and the X-ray source 601 may be configured to rotate synchronously along one or more circular or spiral paths.

Figure 7:
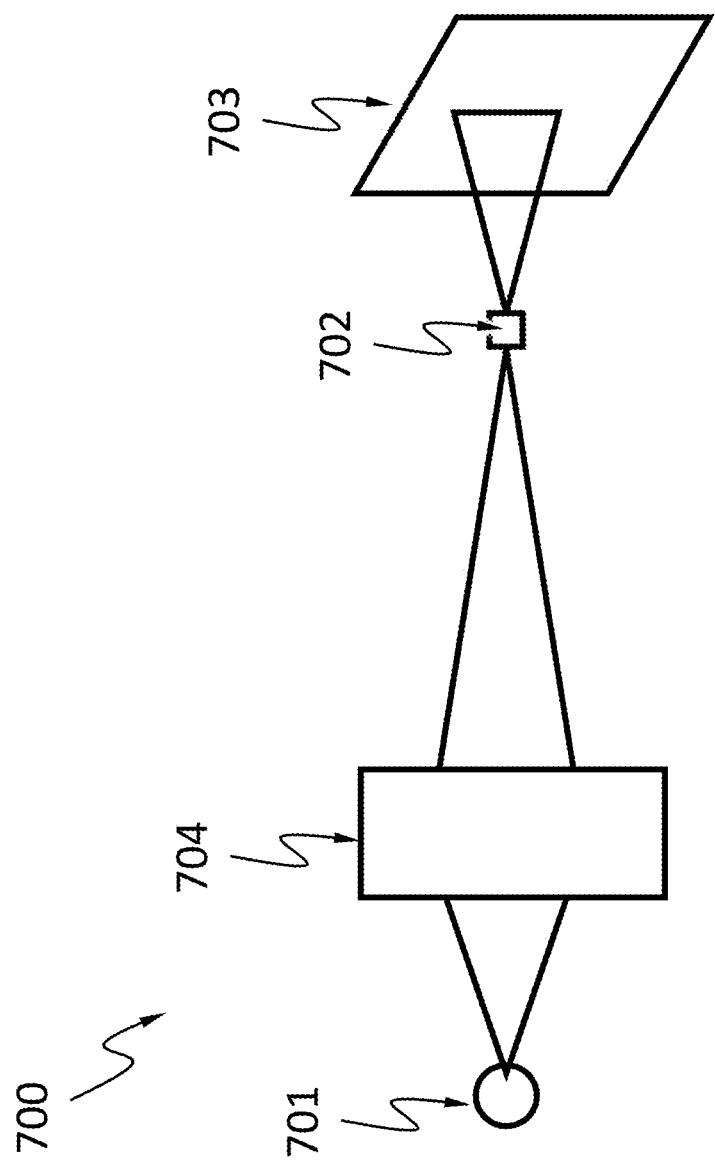
FIG. 7 schematically shows an X-ray microscope or X-ray micro CT 700.

FIG. 7 schematically shows an X-ray microscope or X-ray micro CT 700. The X-ray microscope or X-ray micro CT 700 may include an X-ray source 701, focusing optics 704, and the image sensor 703 being an embodiment of the apparatus 300 described herein, for detecting an X-ray image of a sample 702.

Figure 8:
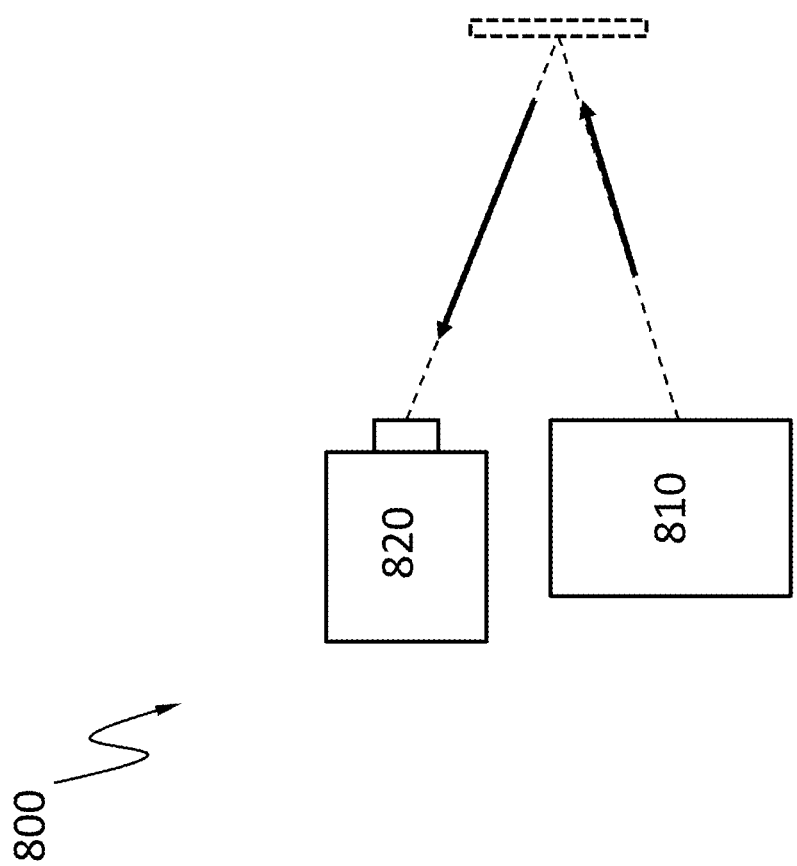
FIG. 8 schematically shows a system suitable for laser scanning, according to an embodiment.

FIG. 8 schematically shows a system 800 suitable for laser scanning, according to an embodiment. The system 800 comprises a laser source 810 and a detector 820 being an embodiment of the apparatus 300 described herein. The laser source 810 may be configured to generate a scanning laser beam. The scanning laser beam may be infrared. In an embodiment, the laser source 810 may perform two-dimensional laser scanning without moving part. The detector 820 may be configured to collect return laser signals after the scanning laser beam bounces off an object, building or landscape and generate electrical signals. The system 800 may further comprise a signal processing system configured to process and analyze the electrical signals generated by the detector 820. In one embodiment, the distance and shape of the object, building or landscape may be obtained. The system 800 may be a Lidar system (e.g., an on-vehicle Lidar).

Figure 9A:
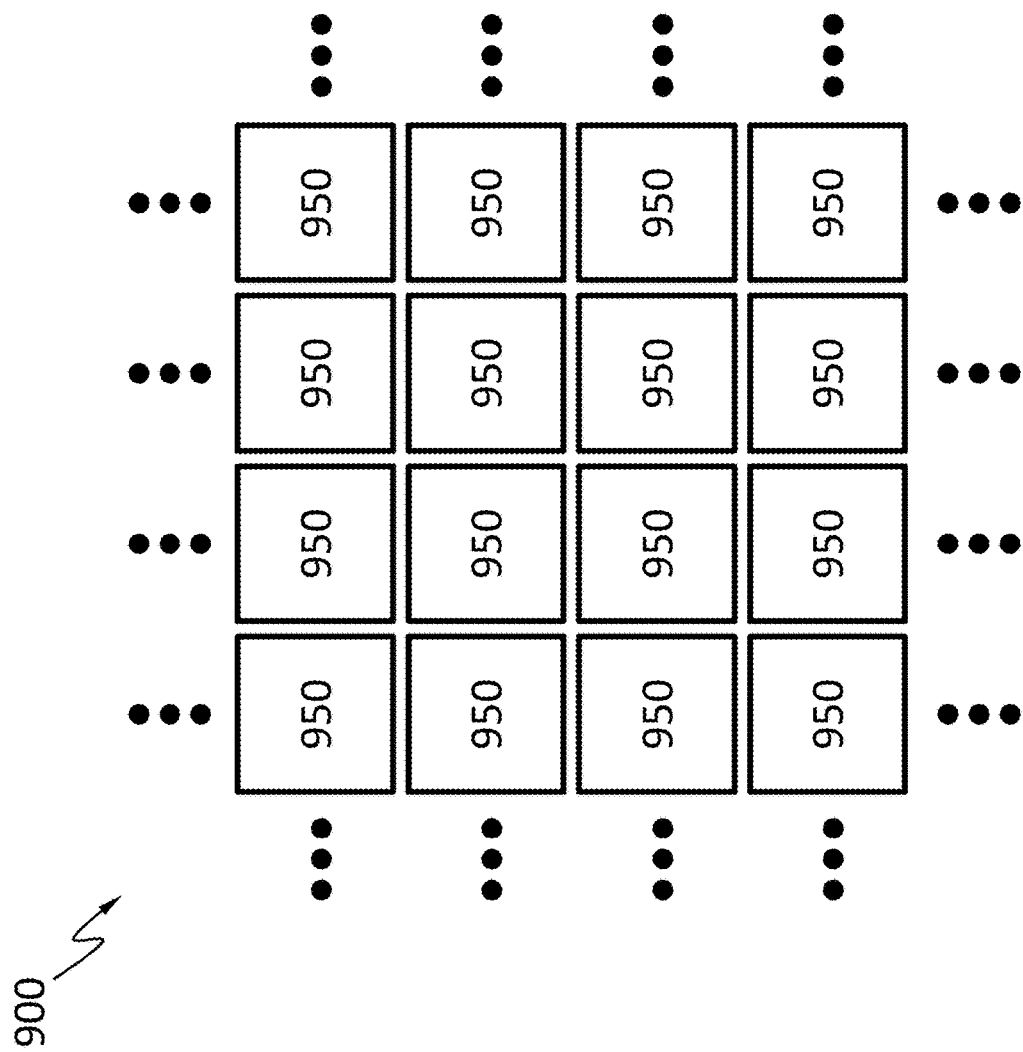
FIG. 9A schematically shows a radiation detector, as an example.

FIG. 9A schematically shows a radiation detector 900, as an example. The radiation detector 900 has an array of pixels 950. The array may be a rectangular array, a honeycomb array, a hexagonal array or any other suitable array. Each pixel 950 is configured to detect radiation from a radiation source incident thereon and may be configured measure a characteristic (e.g., the energy of the particles, the intensity distribution) of the radiation. Each pixel 950 may have its own analog-to-digital converter (ADC) configured to digitize an analog signal representing the energy of an incident radiation particle into a digital signal, or to digitize an analog signal representing the total energy of a plurality of incident radiation particles into a digital signal. The pixels 950 may be configured to operate in parallel. For example, when one pixel 950 measures an incident radiation particle, another pixel 950 may be waiting for a radiation particle to arrive. The pixels 950 may not have to be individually addressable.

Figure 9B:
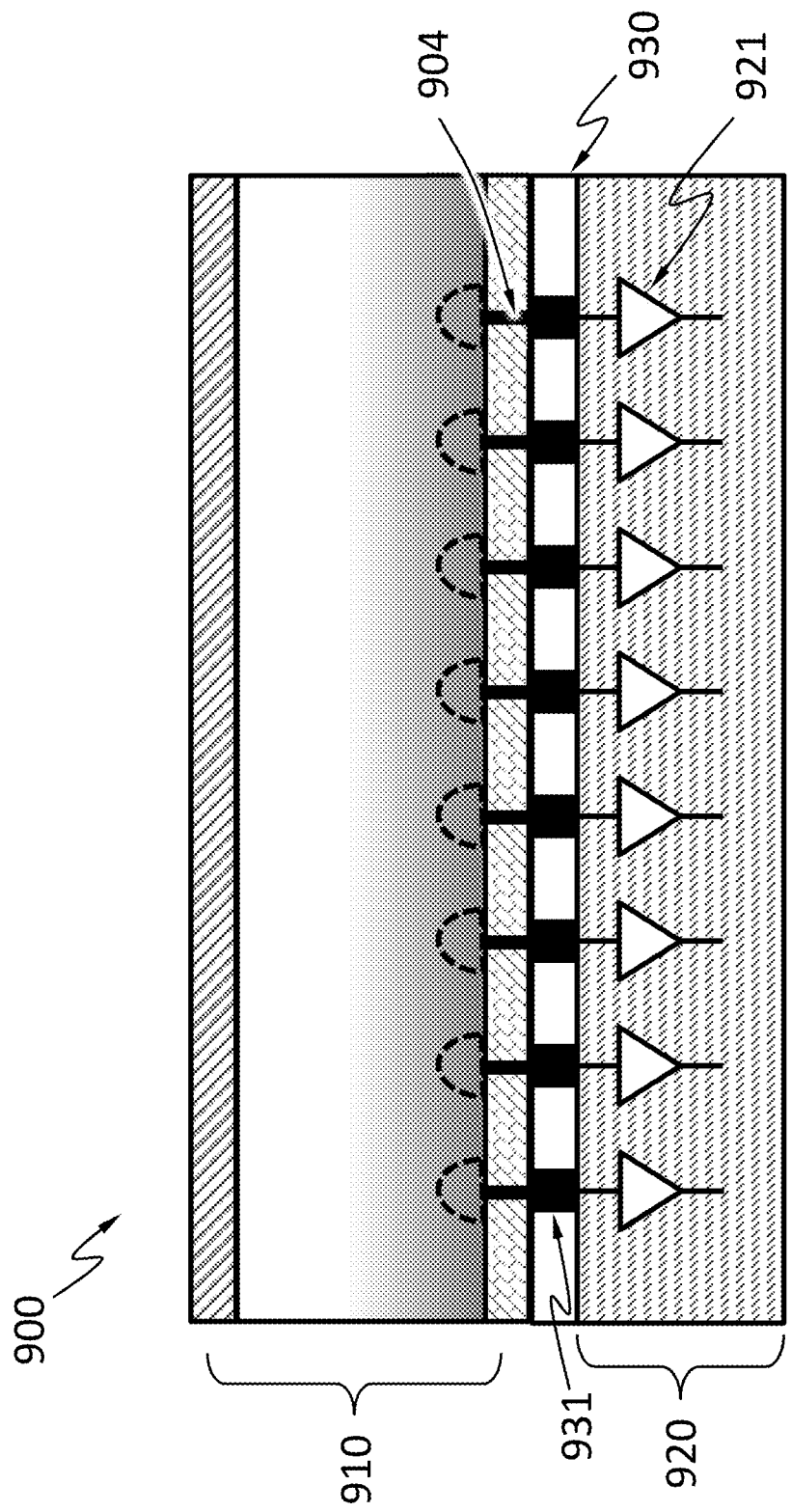
FIG. 9B schematically shows a cross-sectional view of the radiation detector, according to an embodiment.

FIG. 9B schematically shows a cross-sectional view of the radiation detector 900, according to an embodiment. The radiation detector 900 may comprise a radiation absorption layer 910 being an embodiment of the apparatus 300 described herein, and an electronics layer 920 (e.g., an ASIC) for processing or analyzing electrical signals generated by incident radiation or charge carrier avalanche within the radiation absorption layer 910.

The electronics layer 920 may include an electronic system 921 suitable for processing or interpreting the electrical signals. The electronic system 921 may include an analog circuitry such as a filter network, amplifiers, integrators, and comparators, or a digital circuitry such as a microprocessors, and memory. The electronic system 921 may include one or more ADCs. The electronic system 921 may include components shared by the pixels or components dedicated to a single pixel. For example, the electronic system 921 may include an amplifier dedicated to each pixel and a microprocessor shared among all the pixels. The electronic system 921 may be electrically connected to the pixels by vias 931. Space among the vias may be filled with a filler material 930, which may increase the mechanical stability of the connection of the electronics layer 920 to the radiation absorption layer 910. Other bonding techniques are possible to connect the electronic system 921 to the pixels without using vias.

Figure 10A:
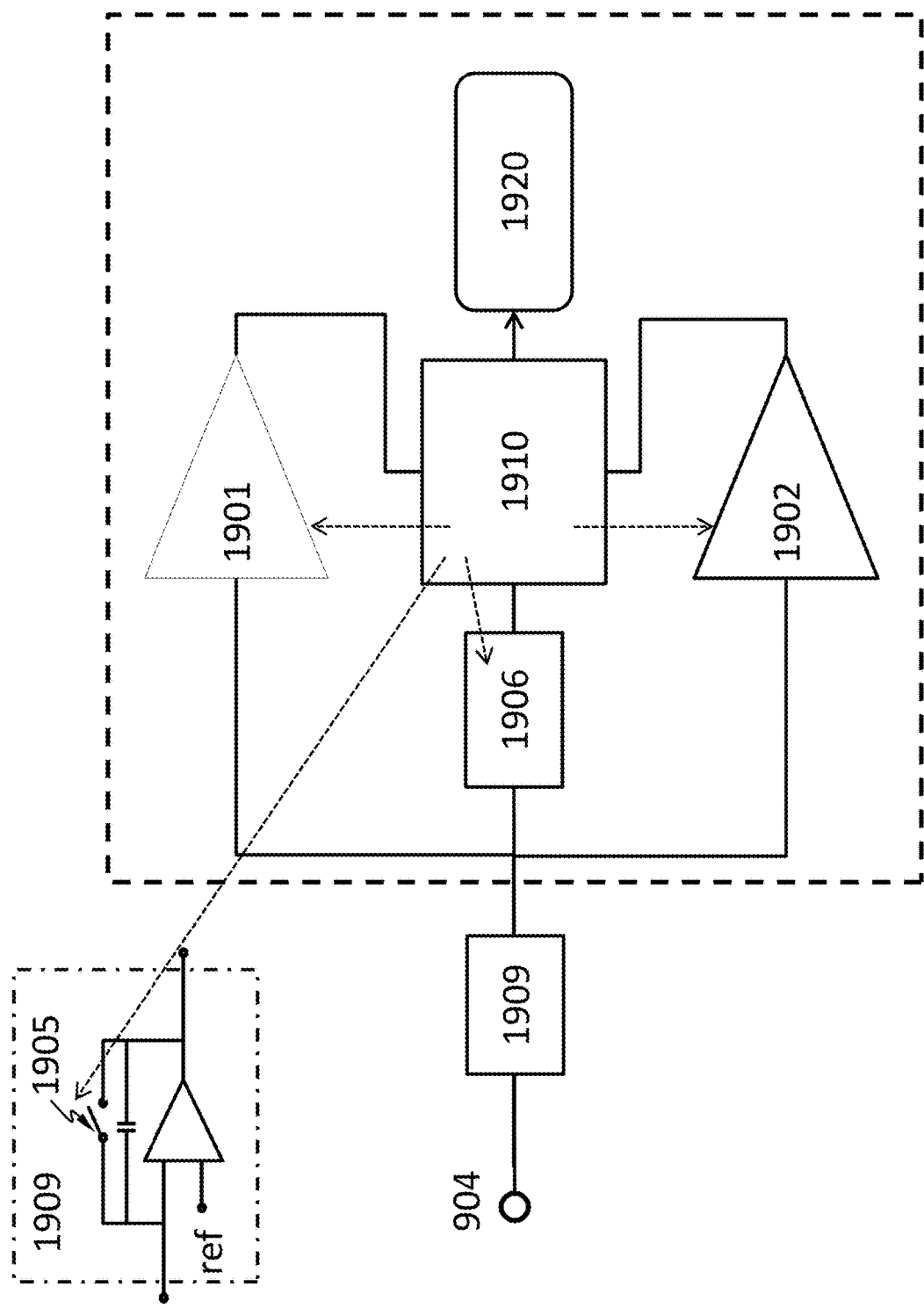
FIG. 10A and FIG. 10B each show a component diagram of the electronic system, according to an embodiment FIG. 11 schematically shows a temporal change of the electric current flowing through the electrode (upper curve) caused by charge carriers generated by an incident radiation particle or charge carrier avalanche in the radiation absorption layer, and a corresponding temporal change of the voltage of the electrode (lower curve).
Figure 10B:
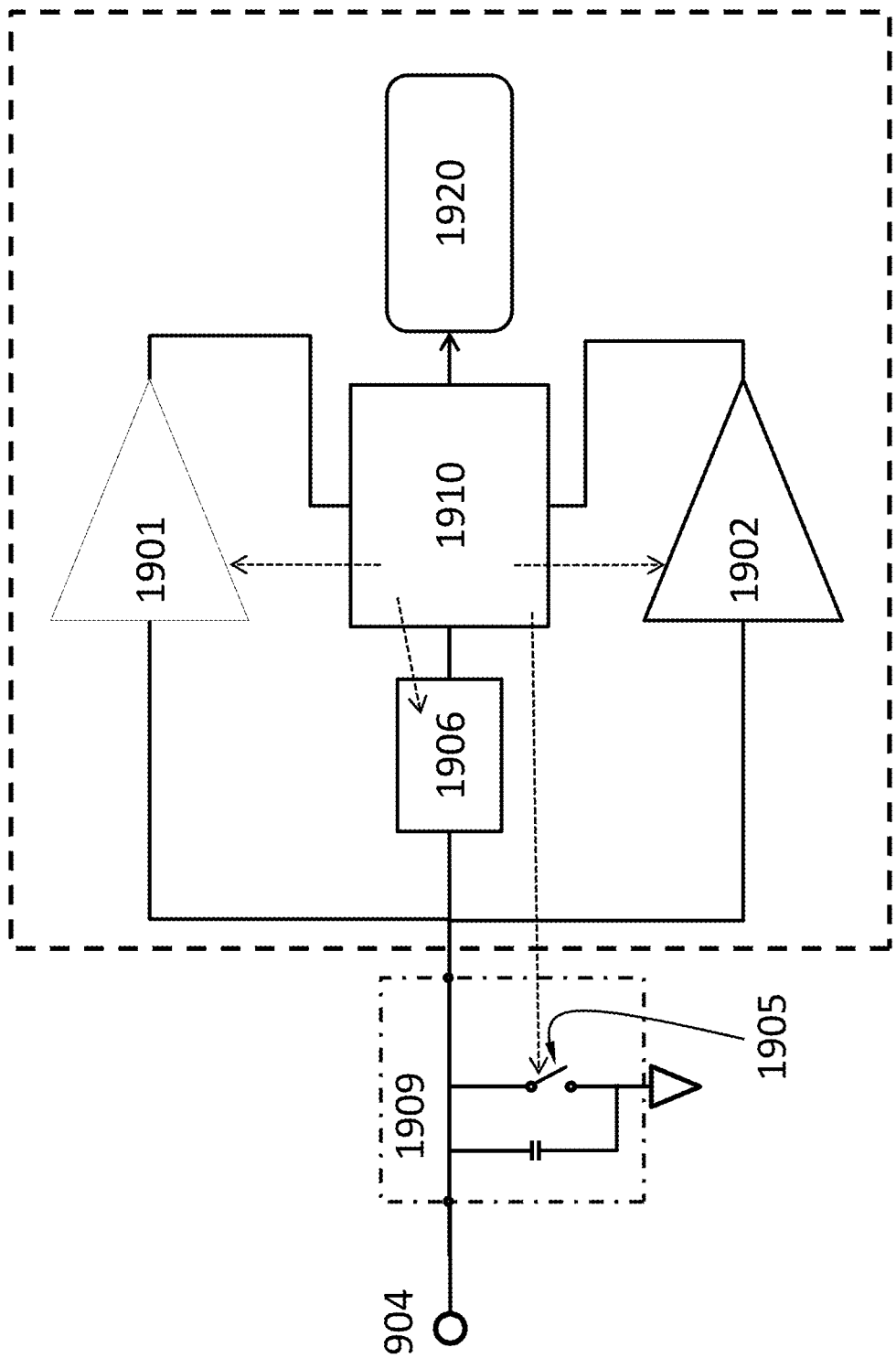

FIG. 10A and FIG. 10B each show a component diagram of the electronic system 921, according to an embodiment. The electronic system 921 may include a first voltage comparator 1901, a second voltage comparator 1902, a counter 1920, a switch 1905, a voltmeter 1906 and a controller 1910.

The first voltage comparator 1901 is configured to compare the voltage of an electrode (e.g., one of the electrodes 904 in FIG. 9B) to a first threshold. The first voltage comparator 1901 may be configured to monitor the voltage directly, or calculate the voltage by integrating an electric current flowing through the electrode over a period of time.

The first voltage comparator 1901 may be controllably activated or deactivated by the controller 1910. The first voltage comparator 1901 may be a continuous comparator. Namely, the first voltage comparator 1901 may be configured to be activated continuously, and monitor the voltage continuously. The first voltage comparator 1901 configured as a continuous comparator reduces the chance that the system 921 misses signals generated directly by an incident radiation particle or by charge carrier avalanche. The first voltage comparator 1901 configured as a continuous comparator is especially suitable when the incident radiation intensity is relatively high. The first voltage comparator 1901 may be a clocked comparator, which has the benefit of lower power consumption. The first voltage comparator 1901 configured as a clocked comparator may cause the system 921 to miss signals generated directly by some incident radiation particles or by charge carrier avalanche. When the incident radiation intensity is low, the chance of missing an incident radiation particle is low because the time interval between two successive radiation particles is relatively long. Therefore, the first voltage comparator 1901 configured as a clocked comparator is especially suitable when the incident radiation intensity is relatively low. The first threshold may be 5-10%, 10%-20%, 20-30%, 30-40% or 40-50% of the maximum voltage one incident radiation particle may generate directly in the radiation absorption layer or after being amplified by avalanche in the radiation absorption layer. The maximum voltage may depend on the energy of the incident radiation particle (i.e., the wavelength of the incident radiation), the material of the radiation absorption layer 910, magnitude of charge carrier avalanche and other factors. For example, the first threshold may be 50 mV, 100 mV, 150 mV, or 200 mV.

The second voltage comparator 1902 is configured to compare the voltage to a second threshold. The second voltage comparator 1902 may be configured to monitor the voltage directly, or calculate the voltage by integrating an electric current flowing through the electrode over a period of time. The second voltage comparator 1902 may be a continuous comparator. The second voltage comparator 1902 may be controllably activated or deactivated by the controller 1910. When the second voltage comparator 1902 is deactivated, the power consumption of the second voltage comparator 1902 may be less than 1%, less than 5%, less than 10% or less than 20% of the power consumption when the second voltage comparator 1902 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident radiation particle may generate directly in the radiation absorption layer or after being amplified in the radiation absorption layer. For example, the second threshold may be 100 mV, 150 mV, 200 mV, 250 mV or 300 mV. The second voltage comparator 1902 and the first voltage comparator 1910 may be the same component. Namely, the system 921 may have one voltage comparator that can compare a voltage with two different thresholds at different times.

The first voltage comparator 1901 or the second voltage comparator 1902 may include one or more op-amps or any other suitable circuitry. The first voltage comparator 1901 or the second voltage comparator 1902 may have a high speed to allow the system 921 to operate under a high flux of incident radiation particle. However, having a high speed is often at the cost of power consumption.

The counter 1920 is configured to register a number of radiation particles reaching the radiation absorption layer. The counter 1920 may be a software component (e.g., a number stored in a computer memory) or a hardware component (e.g., a 4017 IC and a 7490 IC).

The controller 1910 may be a hardware component such as a microcontroller and a microprocessor. The controller 1910 is configured to start a time delay from a time at which the first voltage comparator 1901 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on which electrode is used. The controller 1910 may be configured to keep deactivated the second voltage comparator 1902, the counter 1920 and any other circuits the operation of the first voltage comparator 1901 does not require, before the time at which the first voltage comparator 1901 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 1910 may be configured to activate the second voltage comparator during (including the beginning and the expiration) the time delay. In an embodiment, the controller 1910 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 1910 itself may be deactivated until the output of the first voltage comparator 1901 activates the controller 1910 when the absolute value of the voltage equals or exceeds the absolute value of the first threshold.

The controller 1910 may be configured to cause the number registered by the counter 1920 to increase by one, if, during the time delay, the second voltage comparator 1902 determines that the absolute value of the voltage equals or exceeds the absolute value of the second threshold.

The controller 1910 may be configured to cause the voltmeter 1906 to measure the voltage upon expiration of the time delay. The controller 1910 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 1910 may connect the electrode to the electrical ground by controlling the switch 1905. The switch 1905 may be a transistor such as a field-effect transistor (FET).

In an embodiment, the system 921 has no analog filter network (e.g., a RC network). In an embodiment, the system 921 has no analog circuitry.

The voltmeter 1906 may feed the voltage it measures to the controller 1910 as an analog or digital signal.

Figure 11:
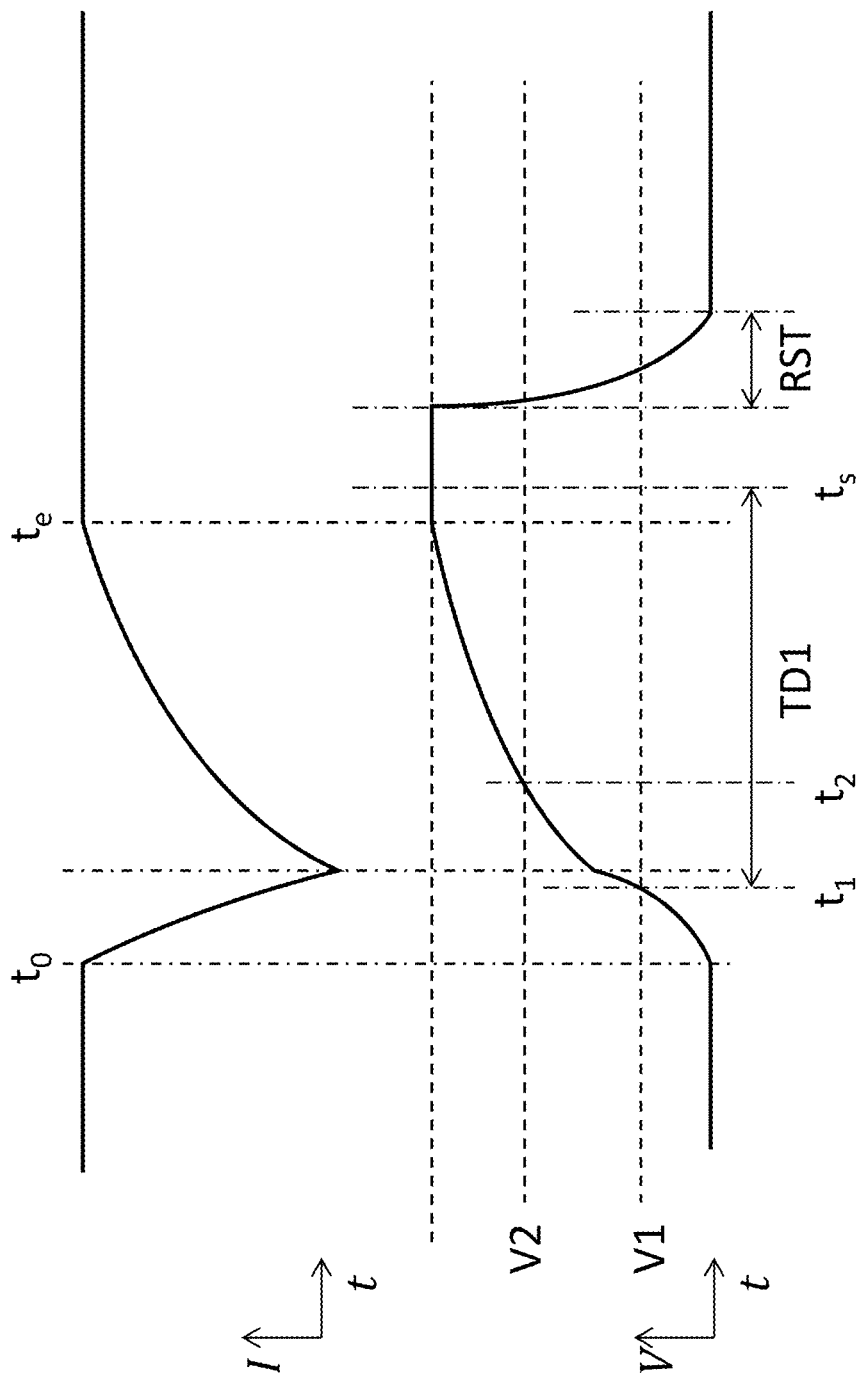

The system 921 may include a capacitor module 1909 electrically connected to the electrode, wherein the capacitor module is configured to collect charge carriers from the electrode. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 11, between $t_0$ to $t_1$, or $t_1$-$t_2$). After the integration period has expired, the capacitor voltage is sampled and then reset by a reset switch. The capacitor module can include a capacitor directly connected to the electrode.

FIG. 11 schematically shows a temporal change of the electric current flowing through the electrode (upper curve) caused by charge carriers generated by an incident radiation particle or charge carrier avalanche in the radiation absorption layer, and a corresponding temporal change of the voltage of the electrode (lower curve). The voltage may be an integral of the electric current with respect to time. At time $t_0$, the radiation particle hits the radiation absorption layer, charge carriers start being generated and being amplified in the radiation absorption layer, electric current starts to flow through the electrode, and the absolute value of the voltage of the electrode starts to increase. At time $t_1$, the first voltage comparator 1901 determines that the absolute value of the voltage equals or exceeds the absolute value of the first threshold V1, and the controller 1910 starts the time delay TD1 and the controller 1910 may deactivate the first voltage comparator 1901 at the beginning of TD1. If the controller 1910 is deactivated before $t_1$, the controller 1910 is activated at $t_1$. During TD1, the controller 1910 activates the second voltage comparator 1902. The term "during" a time delay as used here means the beginning and the expiration (i.e., the end) and any time in between. For example, the controller 1910 may activate the second voltage comparator 1902 at the expiration of TD1. If during TD1, the second voltage comparator 1902 determines that the absolute value of the voltage equals or exceeds the absolute value of the second threshold at time $t_2$, the controller 1910 causes the number registered by the counter 1920 to increase by one. At time $t_e$, all charge carriers generated by the radiation particle drift out of the radiation absorption layer 910. At time $t_s$, the time delay TD1 expires. In the example of FIG. 11, time $t_s$ is after time $t_e$; namely TD1 expires after all charge carriers generated by the radiation particle or charge carrier avalanche drift out of the radiation absorption layer 910. The rate of change of the voltage is thus substantially zero at $t_s$. The controller 1910 may be configured to deactivate the second voltage comparator 1902 at expiration of TD1 or at $t_2$, or any time in between.

The controller 1910 may be configured to cause the voltmeter 1906 to measure the voltage upon expiration of the time delay TD1. In an embodiment, the controller 1910 causes the voltmeter 1906 to measure the voltage after the rate of change of the voltage becomes substantially zero after the expiration of the time delay TD1. The voltage at this moment is proportional to the amount of charge carriers generated by a radiation particle or amplified by the avalanche, which relates to the energy of the radiation particle. The controller 1910 may be configured to determine the energy of the radiation particle based on voltage the voltmeter 1906 measures. One way to determine the energy is by binning the voltage. The counter 1920 may have a sub-counter for each bin. When the controller 1910 determines that the energy of the radiation particle falls in a bin, the controller 1910 may cause the number registered in the sub-counter for that bin to increase by one. Therefore, the system 921 may be able to detect a radiation image and may be able to resolve radiation particle energies of each radiation particle.

After TD1 expires, the controller 1910 connects the electrode to an electric ground for a reset period RST to allow charge carriers accumulated on the electrode to flow to the ground and reset the voltage. After RST, the system 921 is ready to detect another incident radiation particle. Implicitly, the rate of incident radiation particles the system 921 can handle in the example of FIG. 11 is limited by 1/(TD1+RST). If the first voltage comparator 1901 has been deactivated, the controller 1910 can activate it at any time before RST expires. If the controller 1910 has been deactivated, it may be activated before RST expires.

Although X-ray is used as an example of the radiation herein, the apparatuses and methods disclosed herein may also be suitable for other radiation such as infrared light.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
a radiation absorption layer configured to generate charge carriers therein from a radiation particle absorbed by the radiation absorption layer;
a first electrode on the radiation absorption layer;
a second electrode on the radiation absorption layer, the second electrode being opposite from the first electrode;
wherein a geometry of the first electrode is configured to generate an electric field in an amplification region of the radiation absorption layer, the electric field having a field strength sufficient to cause an avalanche of the charge carriers in the amplification region.

2. The apparatus of claim 1, wherein the second electrode is configured to collect charge carriers in the radiation absorption layer.

3. The apparatus of claim 1, wherein the second electrode is planar.

4. The apparatus of claim 1, wherein the second electrode comprises discrete regions.

5. The apparatus of claim 4, wherein the discrete regions of the second electrode extend into the radiation absorption layer.

6. The apparatus of claim 1, wherein the first electrode comprises a tip with a shape of cone, frustum, prism, pyramid, cuboid or cylinder.

7. The apparatus of claim 1, wherein the first electrode is configured to collect the charge carriers generated directly from the radiation particle or by the avalanche.

8. The apparatus of claim 1, wherein the first electrode is configured to concentrate the electric field.

9. The apparatus of claim 1, wherein the first electrode extends into the radiation absorption layer.

10. The apparatus of claim 1, further comprising an outer electrode surrounding the first electrode, and electrically insulated from the first electrode; wherein the outer electrode is configured to shape the electric field in the amplification region.

11. The apparatus of claim 10, wherein the outer electrode is configured not to collect charge carriers.

12. The apparatus of claim 10, wherein the outer electrode comprises discrete regions.

13. The apparatus of claim 1, wherein the amplification region comprises a doped semiconductor.

14. The apparatus of claim 13, wherein the doped semiconductor is in electrical contact with the first electrode.

15. The apparatus of claim 13, wherein the doped semiconductor has a non-zero concentration gradient of a dopant.

16. The apparatus of claim 1, wherein the radiation absorption layer comprises an intrinsic semiconductor region.

* * * * *